United States Patent [19]

Howson

[11] Patent Number: 4,650,850
[45] Date of Patent: Mar. 17, 1987

[54] BIS(DIALKYL AROMATIC ETHER ANHYDRIDE) AND POLYMERS OBTAINED THEREFROM

[75] Inventor: Paul E. Howson, Latham, N.Y.

[73] Assignee: General Electric Company, Schenectady, N.Y.

[21] Appl. No.: 780,856

[22] Filed: Sep. 27, 1985

[51] Int. Cl.$^4$ .............................................. C08G 73/10
[52] U.S. Cl. ...................................... 528/26; 528/125; 528/126; 528/128; 528/172; 528/185
[58] Field of Search ................. 528/26, 125, 126, 128, 528/172, 185

[56] References Cited

U.S. PATENT DOCUMENTS

| | | | |
|---|---|---|---|
| 3,838,097 | 9/1974 | Wirth et al. | 528/185 |
| 4,423,111 | 12/1983 | Lee | 528/185 |
| 4,429,102 | 1/1984 | Evans et al. | 528/185 |
| 4,433,131 | 2/1984 | Bolon et al. | 528/185 |

Primary Examiner—John Kight
Assistant Examiner—M. L. Moore
Attorney, Agent, or Firm—William A. Teoli; James C. Davis, Jr.; James Magee, Jr.

[57] ABSTRACT

Bis(dialkyl aromatic ether anhydride) is provided which can be melt polymerized with organic diamine to high performance polyetherimide having improved heat distortion temperatures.

2 Claims, No Drawings

BIS(DIALKYL AROMATIC ETHER ANHYDRIDE) AND POLYMERS OBTAINED THEREFROM

BACKGROUND OF THE INVENTION

As shown by Heath et al., U.S. Pat. No. 3,847,867, polyetherimides were made by the melt polymerization of aromatic bis(ether anhydride) and organic diamine to provide for the production of injection moldable high performance thermoplastics. It has been found, for example, that when aromatic bis(ether anhydride) such as 2,2-bis[4-(3,4-dicarboxyphenoxy)phenyl]propane dianhydride referred to hereinafter as "BPADA" is melt polymerized with meta-phenylene diamine, polyetherimide is obtained having a Tg in the range of from about 219.6° to 229.1° C. Improved results have been achieved by utilizing other aromatic diamines in place of metaphenylene diamine such as sulfone bis(phenylamine) to improve the Tg and heat distortion temperature of the resulting polyetherimide to satisfy particular applications.

The present invention is based on my discovery that certain bis(dialkyl aromatic ether anhydride) having the formula

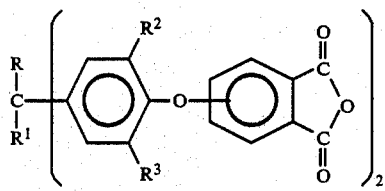

(1)

where R, $R^1$, $R^2$ and $R^3$ are $C_{(1-4)}$ alkyl radicals, hereinafter referred to as "TMBPADA", has been found to provide polyetherimide having a substantially enhanced Tg and heat distortion temperature when melt polymerized with metaphenylene diamine as compared to polyetherimide made by the same procedure from BPADA. Further improvements in Tg and heat distortion temperature can be achieved by melt polymerizing TMBPADA with aromatic diamines such as sulfone bis(phenyl amine) referred to hereinafter as "p2SDAN" to form polyetherimide having Tg's as high as 292.7° C. Surprisingly, although the heat distortion temperature of the resulting polyetherimides are substantially enhanced as the result of using TMBPADA, in accordance with the practice of the present invention, the processability of the resulting polyetherimide is not adversely affected.

STATEMENT OF THE INVENTION

There is provided by the present invention polyetherimides comprising chemically combined ether imide units of the formula,

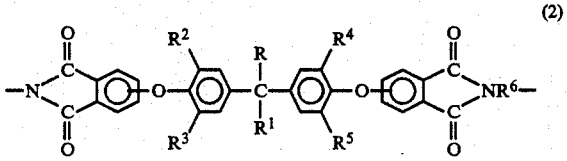

(2)

where $R–R^5$ are the same or different $C_{(1-4)}$ alkyl radicals, $R^6$ is a divalent arylene radical selected from the class consisting of $C_{(6-14)}$ hydrocarbon radicals, substituted $C_{(6-14)}$ hydrocarbon radicals and a divalent radical having the formula, $$-R^7QR^8-,$$

$R^7$ and $R^8$ are the same or different $C_{(6-14)}$ divalent aromatic hydrocarbon radicals or substituted $C_{(6-14)}$ divalent aromatic hydrocarbon radicals, Q is a member selected from

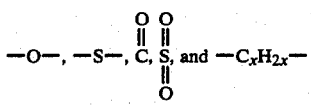

and x is a whole number equal to 1 to 5 inclusive.

Some of the bis(dialkyl aromatic ether anhydrides) of formula (1) which are included by the present invention are the following compounds or mixtures thereof:

2,2-bis[4-(3,4-dicarboxyphenoxy-3,5-dimethyl)phenyl]propane;
2,2-bis[4-(3,4-dicarboxyphenoxy-3,5-diethyl)phenyl]propane;
2,2-bis[4-(3,4-dicarboxyphenoxy-3,5-dipropyl)phenyl]propane;
2,2-bis[4-(3,4-dicarboxyphenoxy-3,5-diisopropyl)phenyl]propane;
2,2-bis[4-(3,4-dicarboxyphenoxy-3,5-dibutyl)phenyl]propane;
2,2-bis[4-(3,4-dicarboxyphenoxy-3,5-diisobutyl)phenyl]propane;
2,2-bis[4-(3,4-dicarboxyphenoxy-3,5-di-tertbutyl)phenyl]propane;
2,2-bis[4-(3,4-dicarboxyphenyl-3,5-dimethyl)phenyl]butane;
3,3-bis[4-(3,4-dicarboxyphenyl-3,5-dimethyl)phenyl]pentane.

Polyetherimides having formula (2) units can be made by effecting reaction between bis(dialkyl aromatic ether anhydride) of formula (1) and organic diamine of the formula $$NH_2R^6NH_2 \qquad (3)$$

where $R^6$ is as previously defined.

There can be employed from about 0.5 to 2 moles of bis(dialkyl aromatic ether anhydride) referred to hereinafter as "aromatic dianhydride" per mole of organic diamine.

Aromatic dianhydride of formula (1) and the organic diamine of formula (3) can be stirred in the presence of a dipolar aprotic organic solvent under ambient conditions to produce a polyamide acid. As taught by Wirth et al., U.S. Pat. No. 3,847,867, polyamide acid solution can be employed as a wire coating enamel by effecting the formula of the polyetherimide on the surface of the wire after being contacted with the polyamide acid solution at temperatures in the range of from about 200°–300° C. It is preferred to effect the melt polymerization of the aromatic dianhydride and organic diamine utilizing an extruder reactor such as shown by Schmidt et al., U.S. Pat. No. 4,443,591, assigned to the same assignee as the present invention and incorporated herein by reference.

The synthesis of the aromatic dianhydride of formula (1) can be achieved by using the procedure shown by Heath et al., U.S. Pat. No. 3,879,428, assigned to the same assignee as the present invention and incorporated herein by reference. Heath et al. effects the nitro displacement of a nitrophthalimide with an alkali diphenoxide to form the corresponding bisimide, followed by the hydrolysis of the bisimides to the dianhydride. A preferred procedure for making the aromatic ether bisimide is by the method shown by Williams, U.S. Pat. No. 4,273,712, also assigned to the same assignee as the present invention and incorporated herein by reference. The Williams procedure involves the displacement of reactive radicals on a phthalimide nucleus with a bisalkali metal phenoxide in the presence of a non-polar solvent and a phase transfer catalyst.

Included by the alkali metal salts of the dihydric phenols utilized in making the aromatic bisimides and aromatic dianhydrides of formula (1) are the alkali metal salts of dihydric phenols or mixtures thereof such as
2,2-bis(4-hydroxy-3,5-dimethylphenyl)propane;
2,2-bis(4-hydroxy-3,5-diethylphenyl)propane;
2,2-bis(4-hydroxy-3,5-dipropylphenyl)propane;
2,2-bis(4-hydroxy-3,5-diisopropylphenyl)propane;
2,2-bis(4-hydroxy-3,5-dibutylphenyl)propane;
2,2-bis(4-hydroxy-3,5-diisobutylphenyl)propane;
2,2-bis(4-hydroxy-3,5-di-t-butylphenyl)propane;
2,2-bis(4-hydroxy-3,5-dimethylphenyl)butane;
3,3-bis(4-hydroxy-3,5-dimethylphenyl)pentane;

Some of the organic diamines which are included in formula (3) are, for example,
m-phenylenediamine;
p-phenylenediamine
4,4'-diaminodiphenylpropane;
4,4'-diaminodiphenylmethane;
benzidine;
4,4'-diaminodiphenyl sulfide;
4,4'-diaminodiphenyl sulfone;
4,4'-diaminodiphenyl ether,
1,5-diaminonaphthalene;
3,3'-dimethylbenzidine;
3,3'-dimethoxybenzidine;
2,4-bis($\beta$-amino-t-butyl)toluene;
bis(p-$\beta$-amino-t-butylphenyl)ether;
bis(p-$\beta$-methyl-o-aminopentyl)benzine;
1,3-diamino-4-isopropylbenzene;
1,2-bis(3-aminopropoxy)ethane;
m-xylylenediamine;
p-xylylenediamine;
2,4-diaminotoluene;
2,6-diaminotoluene;
bis(4-aminocyclohexyl)methane;
3-methylheptamethylenediamine;
4,4-dimethylheptamethylenediamine;
2,11-dodecanediamine;
2,2-dimethylpropylenediamine;
octamethylenediamine;
3-methoxyhexamethylenediamine;
2,5-dimethylhexamethylenediamine;
2,5-dimethylheptamethylenediamine
3-methylheptamethylenediamine;
5-methylnonamethylenediamine;
1,4-cyclohexanediamine;
1,12-octadecanediamine;
bis(3-aminopropyl)sulfide;
N-methyl-bis(3-aminopropyl)amine;
hexamethylenediamine;
heptamethylenediamine;
nonamethylenediamine;
decamethylenediamine;
bis(3-aminopropyl)tetramethyldisiloxane;
bis(4-aminobutyl)tetramethyldisiloxane, etc.,
and mixtures of such diamines.

The polyetherimides of formula (2) can be reinforced with various particulated fillers such as glass fibers, silica fillers, carbon whiskers, up to 50% by weight of the resulting total blend. Reinforcement of polymer can be accomplished prior to polymer formation by effecting polymerization in the presence of filler. Melt blending and solution blending also can be employed.

In order that those skilled in the art will be better able to practice the present invention, the following examples are given by way of illustration and not by way of limitation. All parts are by weight.

EXAMPLE 1

A mixture of 121.55 grams of 2,2'-bis(4-hydroxy-3,5-dimethylphenyl)propane, 68.64 grams of a 50% solution of sodium hydroxide and 40 ml. of water was gently heated and slowly stirred for 1 hour at a temperature of 133° C.

There was added to the mixture 400 ml. of toluene. The mixture was heated and water was removed from the mixture by azeotropic distillation with toluene. The mixture was refluxed for 12 additional hours until water had been completely removed from the mixture.

There was added to the mixture, 6.92 grams (0.0214 moles) of tetrabutylammonium bromide, followed by 176.8 grams (0.858 moles) of 4-nitro-N-methylphthalimide. The mixture was refluxed at 114° C. for 2 hours. It was then allowed to cool slowly to 30° C. After the mixture had cooled to 25° C. there was added 500 ml. of deionized water. Upon stirring, a gold crystalline solid precipitated. After stirring for 5 minutes, the entire mixture was filtered. The filtrate was washed with 500 ml. of water and it was slurried in 500 ml. of acetone and filtered. After drying, there was obtained 178 grams of a gold yellow crystalline product. The product had a melting point of 217° C. The theoretical yield of the product was about 69%. Based on method of preparation and liquid chromatography, and $^{13}$C NMR the product was a bisimide having the following formula:

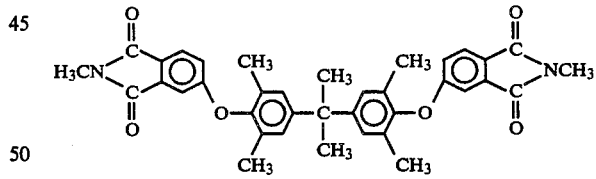

A mixture of 122 grams of the above bisimide, 134.2 grams of a 50% sodium hydroxide solution and 915 ml. of water was heated with stirring under a nitrogen atmosphere to a gentle reflux at 99° C. After 3½ hours, all of the solid bisimide had dissolved. After refluxing the mixture for 22 hours, a nitrogen sparge was introduced to promote the removal of methylamine. The mixture was refluxed and sparging was continued for a total of 90 hours. Water was removed by distillation and replaced with additional water to effect the removal of dissolved methylamine. The tetrasodium salt solution was then added to 3000 ml. of 4-N HCl with stirring at a temperature of 50° C. in a dropwise manner over a period of about 1 hour and 20 minutes. The milky slurry which formed was centrifuged. There was obtained a 98.5% yield of a white product. Based on method of preparation, the product was the corresponding tetraacid of the hydrolyzed bisimide.

A one liter, 3 neck round bottom blask was equipped with a mechanical stirrer, heating mantle, thermometer, reflux condensor and nitrogen bypass. There was refluxed with stirring under a nitrogen atmosphere, 55 grams (0.089 moles) of the above tetra acid, 94 grams of acetic anhydride (0.92 moles) and 295 mls. of toluene. Reflux was continued for 23 hours after which the solution was cooled to 26° C. and filtered to remove some insoluble fines. There was added 600 ml.s of n-heptane to the filtrate. The mixture was heated to reflux resulting in a colorless homogenous solution. Upon cooling the solution, it became cloudy at 57° C. and crystal formation was noticed at 55° C. At 25° C. white crystals were isolated by filtration and dried. There was obtained 28 grams of a white solid. The product melted at 201°-202° C. Proton and $^{13}$C NMR established that the structure was 2,2-bis[4-(3,4-dicarboxyphenoxy-3,5-dimethyl)phenyl]propane. A second crop of 9.8 grams was recovered from the filtrate and was of quality equal to the first crop material. A combined yield of 37.8 grams of 69% of theoretical was realized.

The above dianhydride had a melting point of 201°-202° C.

EXAMPLE 2

A mixture of 20 grams (0.0347 mole) of the dianhydride of Example 1 and 3.75 grams (0.0347 mole) of metaphenylene diamine was charged to a mixing bowl of a Helicone mixer (Model 2CV). The mixture was heated to 300° C. and mixed for 50 minutes. There was obtained a product which was extruded from the Helicone. The resulting amber product had an intrinsic viscosity (I.V.) of 0.68 dl/gm in chloroform at 25° C. and had melt flow characteristics allowing for a good flow performance for easy molding, extrusion and vacuum forming. Based on method of preparation and its NMR spectra, the product was a polyetherimide consisting essentially of chemically combined units of the formula

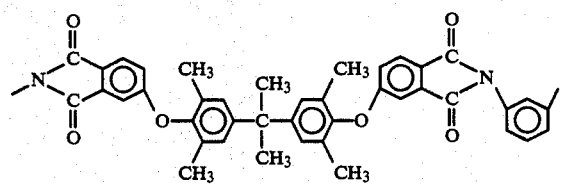

EXAMPLE 3

A mixture of 11.07 grams (0.0192 mole) of the TMBPADA of Example 1, 10 grams of 2,2-bis[4-(3,4-dicarboxyphenoxy)phenyl]propane dianhydride (BPADA), 4.15 grams of (0.0384 mole) of meta-phenylene diamine and 0.1 gram (0.00067 mole) of phthalic anhydride was heated and extruded as described in Example 2 to provide a yellow-green polymer with an I.V. 0.79 in chloroform at 25° C. and excellent melt flow characteristics. The same procedure was repeated, except a 10–90 molar ratio of TMBPADA to BPADA was used. In addition, copolymer was made of equal molar amounts of TMBPADA and sulfone bis(phenylamine) (p²SDAN). The following results were obtained, where m-PDA is meta-phenylene diamine:

| % TMBPADA | % BPADA | % m-PDA | % p²SDAN | I.V. dl/gm, CHCl₃ | Tg Onset | Tg Midpoint | Tg Endpoint |
|---|---|---|---|---|---|---|---|
| 100 | 0 | 100 | | 0.58 | 252.3 | 257.1 | — |
| 50 | 50 | 100 | | 0.79 | 242.3 | 248.1 | 254.1 |
| 25 | 75 | 100 | | 0.55 | 231.8 | 240.6 | 249.3 |
| 10 | 90 | 100 | | 0.91 | 231.1 | 239.8 | 248.7 |
| 3 | 97 | 100 | | 0.41 | 217.9 | 223.1 | 228.1 |
| 100 | 0 | 0 | 100 | 0.6* | 280.9 | 286.8 | 292.7 |
| | | 100* 100 | | 0.48 | 219.6 | 224.3 | 229.1 |

The above results show that polymers made utilizing the bis(dialkylaryl ether anhydrides) of the present invention provide improved Tg's when copolymerized with various organic diamines as compared to polyetherimides shown by the prior art.

Although the above examples are directed to only a few of the very many variables which can be used in the practice of the present invention to make the polyetherimides of formula (2), those skilled in the art would know that a much broader variety of polyetherimides and TMBPADA and methods for making such materials are provided as shown by the description preceding these examples.

What I claim as new and desire to secure by Letters Patent of the United States is:

1. Polyetherimides comprising chemically combined ether imide units of the formula

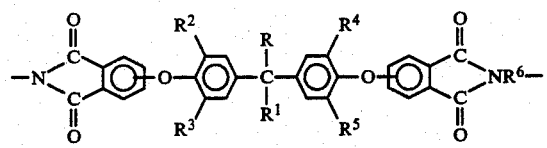

where R–R⁵ are the same or different $C_{(1-4)}$ alkyl radicals, R⁶ is a $C_{(6-14)}$ divalent arylene radical and a divalent radical having the formula,

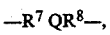

—R⁷QR⁸—,

R⁷ and R⁸ are the same or different $C_{(6-14)}$ divalent aromatic hydrocarbon radicals, Q is a member selected from

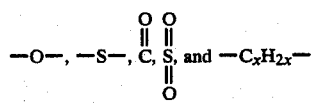

x is a whole number equal to 1 to 5 inclusive.

2. Polyetherimide in accordance with claim 1 consisting essentially of chemically combined units of the formula

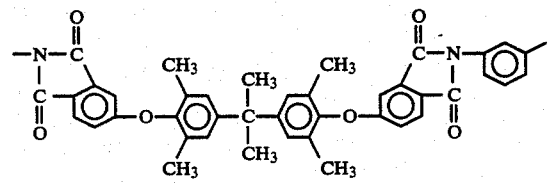

* * * * *